(12) United States Patent
Kwon et al.

(10) Patent No.: US 7,717,842 B2
(45) Date of Patent: May 18, 2010

(54) APPARATUS AND METHOD FOR GENERATING PULSATING NOISE IN AUDIO DEVICE

(75) Inventors: Oh Suk Kwon, Seoul (KR); Jong Woo Kim, Seoul (KR)

(73) Assignee: LG Electronics Inc., Seoul (KR)

( * ) Notice: Subject to any disclaimer, the term of this patent is extended or adjusted under 35 U.S.C. 154(b) by 1427 days.

(21) Appl. No.: 11/037,258

(22) Filed: Jan. 19, 2005

(65) Prior Publication Data
US 2005/0234290 A1    Oct. 20, 2005

(30) Foreign Application Priority Data
Mar. 31, 2004    (KR) .................. 10-2004-0022129

(51) Int. Cl.
*A61M 21/00* (2006.01)
(52) U.S. Cl. ...................................................... 600/28
(58) Field of Classification Search .................. 600/28, 600/27, 545; 128/898, 899, 905; 434/262, 434/236
See application file for complete search history.

(56) References Cited

U.S. PATENT DOCUMENTS

| 4,335,710 A | * | 6/1982 | Williamson | 600/28 |
| 5,914,914 A | * | 6/1999 | Moran | 369/4 |
| 5,954,630 A | * | 9/1999 | Masaki et al. | 600/28 |
| 6,843,765 B2 | * | 1/2005 | Kawamata | 600/28 |
| 7,166,070 B2 | * | 1/2007 | Lawlis et al. | 600/28 |

* cited by examiner

*Primary Examiner*—John P Lacyk
(74) *Attorney, Agent, or Firm*—KED & Associates, LLP

(57) ABSTRACT

An apparatus and method for generating pulsating noise in an audio device are provided. The apparatus and method mix audio signals processed by an audio play operation with pulsating noise generated by a pulsating noise generator if a brain wave induction mode is set in an audio device and output a result of the mixing operation through wired or wireless speaker. Therefore, a user can efficiently experience brain wave induction action based on the pulsating noise while he/she hears audio from the speaker.

21 Claims, 3 Drawing Sheets

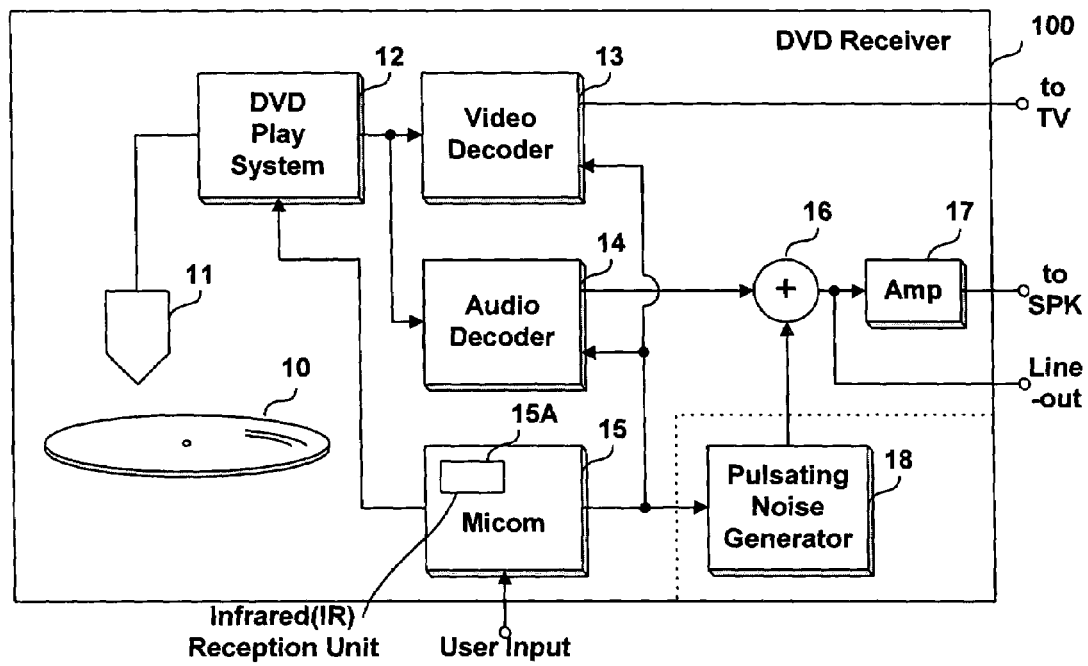

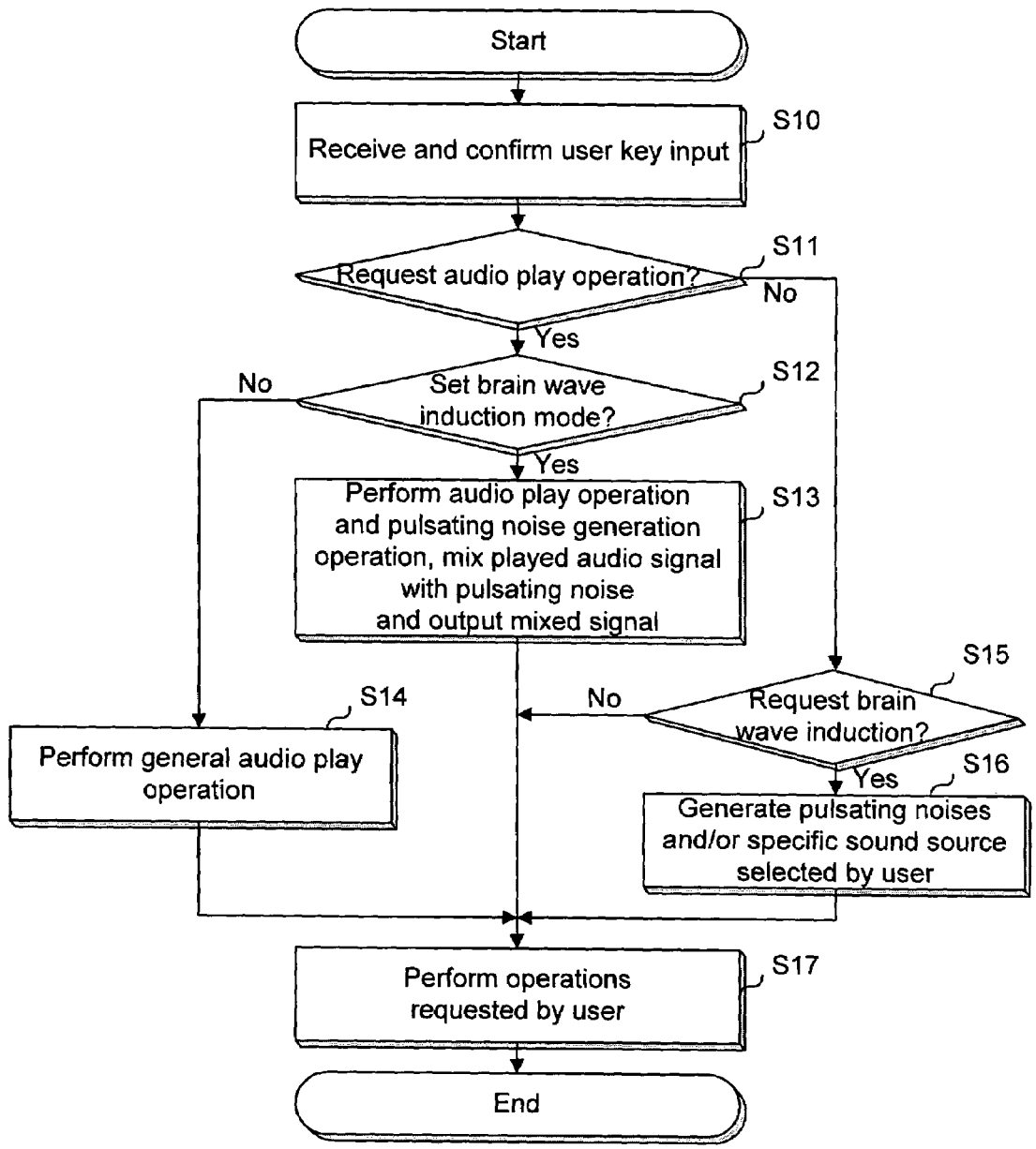

APPARATUS AND METHOD FOR GENERATING PULSATING NOISE IN AUDIO DEVICE

BACKGROUND OF THE INVENTION

1. Field of the Invention

The invention relates to an apparatus and method for generating pulsating noise in an audio device.

2. Background of the Related Art

Generally, human brain waves are low frequency, around 30 Hz, and can be classified into types based on human mental activity. For example, as shown in FIG. 1, when human mental activity is operating normally, beta waves having a frequency range of about 15~30 Hz are generated. If a person continuously engages in a mental activity associated with beta waves, he/she is easily exhausted.

Alpha waves having a frequency range of about 8~14 Hz are generated when a person rests, for example, through meditation and concentrates on something. Theta waves having a frequency range of about 4~7 Hz are generated when a person displays his/her learning ability or is in light sleep and drowsiness. Delta waves having a frequency range of about 0.5~3 Hz are generated when a person is in the deepest stage of sleep. Also, gamma waves of more than about 30 Hz are generated when a person is extremely excited or gets angry.

Brain wave induction technology involves artificially synchronizing human brain waves to a desired frequency. Namely, brain wave induction technology employs Frequency Following Effect (FFE) of the human brain, in which, when a person is visually or aurally stimulated at a predetermined frequency, a brain wave corresponding to the predetermined frequency is induced. Accordingly, when a person works under a strain or feels stress due to his/her routine work, he/she can get a refreshment effect as alpha waves having the frequency range of about 8~14 Hz is induced putting his/her brain in a state similar to when he/she rests and relaxes both mentally and physically.

Optical glasses are used in most brain wave inductors. For example, LEDs with a relatively high light emission are turned on and off ten times per second to induce Alpha wave of about 10 Hz.

Also, technologies inducing brain waves by stimulating auditory senses are classified into, for example, those using a Binaural Beat, those using a Modulated Noise, and those using a Pulsating Noise. Technologies using Binaural Beats are operated such that, when sounds having different frequencies 'f' and 'f+a' in sinusoidal waves are applied to the right and left ears, respectively, brain waves corresponding to a frequency difference 'a' is induced. For example, when sounds at frequencies of 200 Hz and 210 Hz are applied to the right and left eats, respectively, alpha waves of 10 Hz are induced in the brain. However, since sounds having different frequencies in sinusoidal waves should be applied directly to the right and left ears, respectively, users must utilize stereo earphones or a headphone.

Pulsating noise technology operates in such a way that a specific noise or pure sound of a specific frequency is pulsated to provide optical stimulation of a predetermined frequency to users to induce, for example, alpha waves. Therefore, users can use a speaker rather than stereo earphones or a headphone.

Recently, a need to experience brain wave induction phenomenon using pulsating noise has been requested while a user listens to audio through a speaker without wearing earphones or a headphone. However, previously there has been no solution.

SUMMARY OF THE INVENTION

An object of the invention is to solve at least the above problems and/or disadvantages and to provide at least the advantages described hereinafter.

In order to achieve at least the above objects, in whole or in part, and in accordance with the purposes of the invention, as embodied and broadly described herein, there is provided an apparatus for generating pulsating noise in an audio device in accordance with an embodiment of the invention that includes an audio unit including an audio signal processing unit for processing audio data, a pulsating noise generator for generating pulsating noise at a predetermined frequency, and a mixing unit, wherein the mixing unit mixes an audio signal processed by the audio signal processing unit with the pulsating noise generated by the pulsating noise generator.

To further achieve at least the above objects, in whole or in part, and in accordance with the purposes of the invention, as embodied and broadly described herein, there is provided a method for generating pulsating noise in an audio device in accordance with an embodiment of the invention that includes confirming whether a brain wave induction mode is set if an audio play operation is requested, generating pulsating noise if there is a confirmation indicating that the brain wave induction mode is set, and mixing the pulsating noise with an audio signal processed by the audio play operation.

To further achieve at least the above objects, in whole or in part, and in accordance with the purposes of the invention, as embodied and broadly described herein, there is provided an apparatus for generating pulsating noise for use with an audio device in accordance with an embodiment of the invention that includes a pulsating noise generator configured to generate pulsating noise at a predetermined frequency, the pulsating noise being designed to induce a brain wave of a user corresponding to the predetermined frequency, and electronic communication means for providing electronic communication with an audio device.

Additional advantages, objects, and features of the invention will be set forth in part in the description which follows and in part will become apparent to those having ordinary skill in the art upon examination of the following or may be learned from practice of the invention. The objects and advantages of the invention may be realized and attained as particularly pointed out in the appended claims.

BRIEF DESCRIPTION OF THE DRAWINGS

The invention will be described in detail with reference to the following drawings in which like reference numerals refer to like elements wherein:

FIG. 1 is a chart illustrating categories of human brain waves based on frequency bands;

FIG. 2 is a block diagram of an apparatus for generating pulsating noise in an audio device according to an embodiment of the invention;

FIG. 4 is a flow chart of a method for generating pulsating noise in an audio device according to an embodiment of the invention.

DETAILED DESCRIPTION OF PREFERRED EMBODIMENTS

Figure 3:
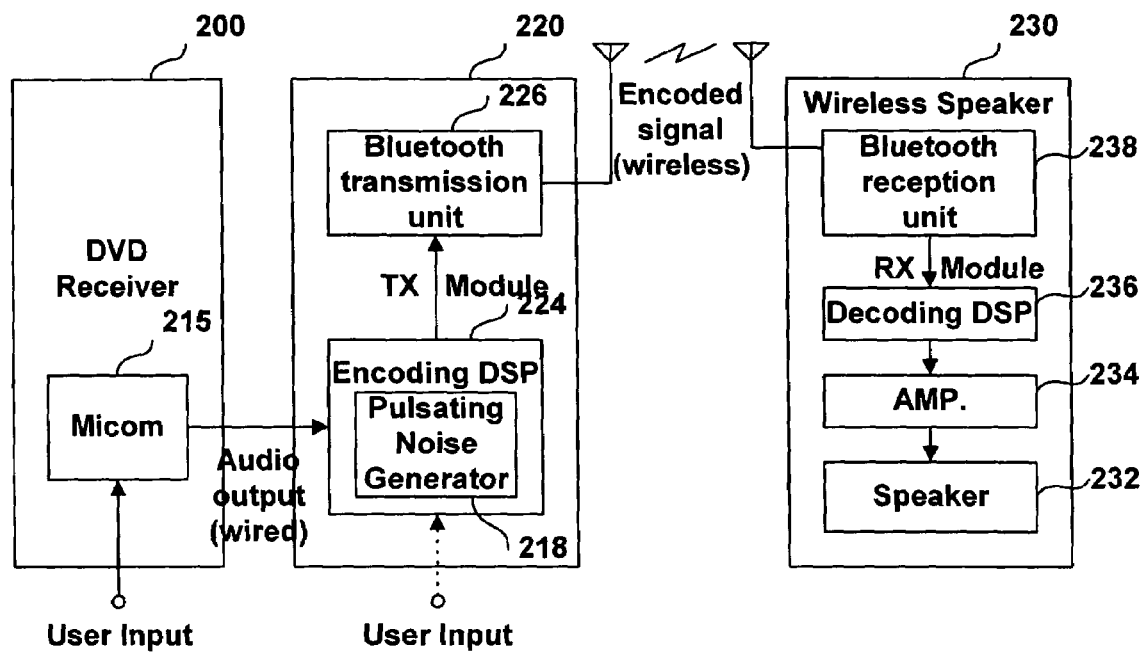
FIG. 3 is a block diagram of an apparatus combining a transmission module with an apparatus for generating pulsating noise according to an embodiment of the invention.

Now, an apparatus and method for generating pulsating noise according to embodiments of the invention will be described in detail with reference to the drawings, in which like reference numerals have been used to designate like elements. An apparatus and method for generating pulsating noise according to embodiments of the invention can be applied to various type audio devices that read out audio signals from a recording medium, such as a DVD, and output them through a wired or wireless speaker. An audio device 100 adopting the invention, such as a DVD receiver, is shown in FIG. 2, and includes an optical disc 10, an optical pick-up 11, a DVD play system 12, a video decoder 13, an audio decoder 14, a microcomputer 15, a mixer 16, an amplifier 17, and a pulsating noise generator 18.

The pulsating noise generator 18 may be included in the audio device 100, or may be a separate device for universality which can be connected to the audio device 100. In the latter case, the pulsating noise generator 18 may include a device for receiving a user input, for example, an infrared (IR) reception unit 15A, such that a user can directly control the pulsating noise generator 18. Also, the pulsating noise generator 18 may input commands from the audio device 100 to control pulsating noise generation.

According to another embodiment of the invention, a pulsating noise generator 218, as shown in FIG. 3, may be mounted within a transmission module 220, for example, a Local Area wireless communication apparatus, such as a BLUETOOTH® transmission module. In this case, the transmission module 220 can control operation of the pulsating noise generator 218 through a command based on user direct input or command input from an audio device 200, such as a DVD receiver.

As shown in FIG. 3, the DVD receiver 200 includes a microcomputer 215 and is configured to receive user input and output an audio output signal to the transmission module 220. The transmission module 220 includes the pulsating noise generator 218 as part of an encoding DSP 224, which communicates with a transmission unit 226, for example, a BLUETOOTH® transmission unit, via a TX module. The transmission module 220 is in wireless communication with a wireless speaker 230, which includes a reception unit 238, such as a BLUETOOTH® reception unit, in communication via a RX module with a Decoding DSP 236, an amplifier 234, and a speaker 232.

The pulsating noise generator 18 or 218 generates pulsating noise of a predetermined frequency band if a user requests an induction operation for a specific brain wave during an audio play operation or regardless of an audio play operation. Also, while audio is not being played, the pulsating noise generator 18 or 218 may generate pulsating noise of a predetermined frequency band according to a user request and, at the same time, generate one of a plurality of sound sources, for example, a raining sound, a stream sound, or a bird sound, previously stored in a memory. Accordingly, a user may sleep or meditate based on the pulsating noise and/or various sound sources generated as indicated above.

FIG. 4 is a flow chart of a method for generating pulsating noise in an audio device according to an embodiment of the invention. The method for generating pulsating noise in an audio device according to an embodiment of the invention is discussed with reference to the apparatus shown in FIG. 2. However, it should be understood that the method may be implemented with any type audio device.

As shown in FIG. 4, when a key input is selected by a user, the microcomputer 15 confirms a value corresponding to the key input, in step S10. Then, if an audio play operation is requested by the user through key buttons, for example, in a remote controller, in step S11, the microcomputer 15 confirms that a brain wave induction mode has been set, in step S12.

If the brain wave induction mode has been set based on the result of the confirmation, the microcomputer 15 controls the DVD play system 12, the video decoder 13, and audio decoder 14 to perform an audio play operation and simultaneously controls the pulsating noise generator 18 to perform pulsating noise operation, in step S13.

Here, the mixer 16 mixes the audio signal processed by the audio decoder 14 with the pulsating noise of a predetermined frequency band generated by the pulsating noise generator 18 to output the mixed signal to the amplifier 16. The amplifier 16 amplifies the mixed signal to output it to a speaker.

Also, the mixed signal may be output to a wireless speaker through, for example, a transmission module, such as a BLUETOOTH® transmission module, connected to the line-out. In this case, the transmission module encodes the mixed signal in a predetermined format to perform wireless transmission, for example, Local Area Wireless Communication, and transmits it in a wireless transmission manner. In the case of a BLUETOOTH® module, a BLUETOOTH® reception module receives and decodes the wireless signal from the transmission module and amplifies it to the speaker.

According to embodiments of the invention, because the pulsating noise is a signal having a low frequency band even less than that of a general audio signal, it does not affect the audio signal mixed by the mixer 16. Further, if the brain wave induction mode has not been set in step S12, the microcomputer 15 controls operation of the DVD play system 12 the video decoder 13, and audio decoder 14, and operation of the pulsating noise generator 18 is omitted, in step S14, such that only a general audio play operation is performed.

On the other hand, when a brain induction operation is requested by a user in a state in which an audio play operation is not requested, in step S15, the microcomputer 15 controls the pulsating noise generator 18 such that pulsating noise of a predetermined frequency band is generated and/or one of various sound sources, such as a raining sound, a stream sound, or a bird sound, which are previously stored in a memory, is generated based on a user's selection, in step S16.

Meanwhile, as shown in FIG. 3, in the case that the pulsating noise generator is mounted within an encoding DSP of a transmission module, the encoding DSP mixes the pulsating noise generated from the core with audio signal output from the audio device, such as the DVD receiver.

The apparatus and method for generating pulsating noise in an audio device according to embodiments of the invention provide at least the following advantages.

The apparatus and method for generating pulsating noise in an audio device according to embodiments of the invention ate capable of reading out audio signals from a recording medium, such as a Digital Versatile/Video Disc (DVD), and outputting the audio signals together with pulsating noise of a predetermined frequency band for brain wave induction through a wired or wireless speaker.

The apparatus and method for generating pulsating noises according to embodiments of the invention are capable of outputting pulsating noises and audio signals together through a speaker in a general audio device. Accordingly, the user can naturally feel brain wave induction phenomenon, receiving pulsating noise while he/she hears audio from a speaker. Also, a user can effectively sleep or meditate using specific sound sources.

The foregoing embodiments and advantages are merely exemplary and are not to be construed as limiting the invention. The present teaching can be readily applied to other types of apparatuses. The description of the invention is intended to be illustrative, and not to limit the scope of the claims. Many alternatives, modifications, and variations will be apparent to those skilled in the art. In the claims, means-plus-function clauses are intended to cover the structures described herein as performing the recited function and not only structural equivalents but also equivalent structures.

What is claimed is:

1. An apparatus for generating pulsating noise in an audio device, comprising:
   an audio signal processor configured to provide an audio signal from a DVD;
   a pulsating noise generator configured to generate pulsating noise at a predetermined frequency; and
   a mixing device that mixes the audio signal from the audio signal processor with the pulsating noise from the pulsating noise generator and provides the mixed output signal.

2. The apparatus as set forth in claim 1, wherein the pulsating noise generator is further configured to generate various sound sources.

3. The apparatus as set forth in claim 1, wherein the pulsating noise generator is mounted within a communication transmission module.

4. The apparatus as set forth in claim 3, wherein the communication transmission module comprises a local area wireless transmission module.

5. The apparatus as set forth in claim 3, wherein the pulsating noise generator is controlled by a user input through an input device.

6. The apparatus as set forth in claim 3, further comprising a controller configured to control operation of the pulsating noise generator based on a user request.

7. An audio device comprising:
   an audio signal processor configured to provide an audio signal from a DVD;
   a pulsating noise generator configured to generate pulsating noise at a predetermined frequency; and
   a mixing device that mixes the audio signal from the audio signal processor with the pulsating noise from the pulsating noise generator and provides the mixed output signal.

8. A DVD player comprising an audio device including:
   an audio signal processor configured to provide an audio signal from a DVD;
   a pulsating noise generator configured to generate pulsating noise at a predetermined frequency; and
   a mixing device that mixes the audio signal from the audio signal processor with the pulsating noise from the pulsating noise generator and provides the mixed output signal.

9. A method for generating pulsating noise in an audio device, comprising:
   determining, by a controller, whether an audio play operation is requested;
   determining, by the controller, whether a brain wave induction mode is set;
   providing an audio signal from a DVD when the audio play operation is requested;
   generating pulsating noise when the brain wave induction mode is set; and
   mixing the pulsating noise with the audio signal from the DVD to provide an output signal.

10. The method as set forth in claim 9, further comprising:
    receiving a user request via an input device; and
    confirming the user request before the determinings.

11. The method as set forth in claim 9, further comprising:
    generating pulsating noises and/or specific sound sources selected by a user, when the brain wave induction operation is requested.

12. The method as set forth in claim 9, wherein the method is implemented in an audio device of a DVD player.

13. An apparatus comprising:
    a device to provide an audio signal from a DVD;
    a pulsating noise generator to generate pulsating noise at a predetermined frequency, the pulsating noise being designed to induce a brain wave of a user corresponding to the predetermined frequency;
    a device to combine the audio signal and the pulsating noise and provide an output signal; and
    an electronic communication device that provides electronic communication of the output signal from the apparatus.

14. The apparatus as set forth in claim 13, wherein the electronic communication device comprises a wireless communication device to wirelessly transmit the output signal from the apparatus.

15. The method as set forth in claim 11, wherein generating pulsating noises and/or specific sound sources selected by the user, when the brain wave induction operation is requested comprises concurrently generating pulsating noises and specific sound sources selected by the user, when the brain wave induction operation is requested.

16. An audio device comprising:
    a device to provide an audio signal from a DVD;
    a pulsating noise generator to generate pulsating noise at a predetermined frequency, the pulsating noise being designed to induce a brain wave of a user corresponding to the predetermined frequency;
    a device to combine the audio signal and the pulsating noise and provide an output signal; and
    an electronic communication device that provides electronic communication of the output signal from the apparatus.

17. A DVD player comprising an audio device including:
    a device to provide an audio signal from a DVD;
    a pulsating noise generator to generate pulsating noise at a predetermined frequency, the pulsating noise being designed to induce a brain wave of a user corresponding to the predetermined freguency;
    a device to combine the audio signal and the pulsating noise and provide an output signal; and
    an electronic communication device that provides electronic communication of the output signal from the apparatus.

18. The apparatus as set forth in claim 1, further comprising a speaker to output the mixed output signal.

19. The apparatus as set forth in claim 1, further comprising a transmission unit to wirelessly transmit the mixed output signal.

20. The method as set forth in claim 9, further comprising a speaker to output the output signal from the audio device.

21. The method as set forth in claim 9, further comprising a transmission unit to wirelessly transmit the output signal from the audio device.

* * * * *